United States Patent

Hell et al.

[11] Patent Number: 6,164,820
[45] Date of Patent: Dec. 26, 2000

[54] X-RAY EXAMINATION SYSTEM PARTICULARY FOR COMPUTED TOMOGRAPHY AND MAMMOGRAPHY

[75] Inventors: Erich Hell; Detlef Mattern, both of Erlangen; Peter Schardt, Roettenbach, all of Germany

[73] Assignee: Siemens Aktiengesellschaft, Munich, Germany

[21] Appl. No.: 09/306,335

[22] Filed: May 6, 1999

[30] Foreign Application Priority Data

May 6, 1998 [DE] Germany ............... 198 20 197

[51] Int. Cl.⁷ ...................................... H01J 35/24
[52] U.S. Cl. ..................... 378/193; 378/135; 378/119
[58] Field of Search ............................ 378/144, 125, 378/119, 193, 135, 136

[56] References Cited

U.S. PATENT DOCUMENTS

| | | | |
|---|---|---|---|
| 2,111,412 | 3/1938 | Ungelenk | 378/135 |
| 2,900,543 | 8/1959 | Heuse | 378/130 |
| 4,788,705 | 11/1988 | Anderson | 378/121 |
| 4,993,005 | 2/1991 | Rand et al. | 378/125 |
| 5,086,442 | 2/1992 | Gemmel et al. | 378/132 |
| 5,291,538 | 3/1994 | Burke et al. | 378/135 |
| 5,581,591 | 12/1996 | Burke et al. | 378/135 |
| 5,592,526 | 1/1997 | Daikoku et al. | 378/135 |
| 5,883,936 | 3/1999 | Hell et al. | 378/125 |
| 6,084,942 | 7/2000 | Hell et al. | 378/135 |

*Primary Examiner*—David P. Porta
*Assistant Examiner*—Drew A. Dunn
*Attorney, Agent, or Firm*—Schiff Hardin & Waite

[57] ABSTRACT

X-ray examination installation, particularly for computed tomography for mammography, has a rotating bulb x-ray tube with a cathode-side drive as its x-ray source, with the tube being oriented so that its anode faces toward the exposure side or actuation side of the system. The distance between the x-ray beam exit window of the tube, and the exposure side or actuation side of the system, thus is made small.

9 Claims, 2 Drawing Sheets

X-RAY EXAMINATION SYSTEM PARTICULARY FOR COMPUTED TOMOGRAPHY AND MAMMOGRAPHY

BACKGROUND OF THE INVENTION

1. Field of the Invention

The invention is directed to an x-ray examination system having an x-ray source, particularly for computed tomography and for mammography.

2. Description of the Prior Art

In computed tomography, the physician would like to have the exposure plane, i.e. the plane of the body layer to be exposed, and thus the focal spot of the x-ray source, as close as possible to the actuation side of the gantry, i.e., that side of the gantry at which the physician is located for preparation for the exposure and possibly during the implementation of an examination. The actuation side of the gantry is usually provided with control and/or display elements.

Similarly, there is also a desire in mammography to bring the focal spot of the x-ray source as close as possible to a plane containing the sternum of a patient to be examined, and thus over the free end—representing the exposure side of the x-ray examination system—of a support provided for the breast of the patient, in order to be able to irradiate the tissue to be examined as completely as possible with the x-rays emanating from the focal spot, i.e. including the base of the breast, i.e. that region of the breast that forms the transition to the rib cage.

Since the x-rays emanating from the focal spot of the x-ray source leave the x-ray source through its radiation exit window, the above desires mean that the beam exit window of the x-ray source should be located as close as possible to the operating or exposure side of the x-ray examination system. A beam exit window that is located close to the end face of the x-ray source is in fact possible given x-ray tubes with a stationary anode (standing anode) operated as a single-pole tube, however, x-ray sources in computed tomography as well as in mammography usually contain rotating anode x-ray tube.

Due to the necessity, extremely high tube voltage, an x-ray tube utilized in x-ray sources provided for computed tomography is conventionally a two-pole x-ray tube and thus has an insulator at the anode side as well as at the cathode side. The length of this insulator determines the minimum spacing of the beam exit window from the corresponding end of the x-ray source. For this reason, x-ray tubes utilized in computer tomography are desired, to the extent possible, to reduce the overall structural length of the x-ray source, including insulators.

There are specific rotating anode x-ray tubes for x-ray sources provided for mammography that are operated as single-pole tubes, the drive being located at that side of the anode facing away from the patient. The spacing of the beam exit window from the end of the x-ray source at the cathode side is determined in such arrangements by the focal head length and the spacing between the cathode and the anode of the rotating anode x-ray tubes as well as by the spacing between the cathode-side end of the rotating anode x-ray tube and the cathode-side end of the x-ray source.

German OS 196 31 899 (corresponding to U.S. Pat. No. 5,883,936), German OS 41 08 591 and U.S. Pat. No. 4,788,705 disclose rotating bulb tubes, however, nothing can be derived from these publications about the installation position of the disclosed rotating bulb tubes in an x-ray examination system.

In mammography as well as in computed tomography, there is thus a need for an x-ray source having a beam exit window located extremely close to the actuation side or the exposure side.

SUMMARY OF THE INVENTION

An object of the present invention is to provide an x-ray examination system of the type initially described, particularly for mammography and computed tomography, wherein the spacing of the beam exit window of the x-ray source from the actuation side or exposure side of the x-ray examination system can be reduced compared to known systems.

This object is inventively achieved in an x-ray source containing a rotating bulb tube with a cathode-side drive, the tube having an anode which faces toward the exposure or actuation side of the system.

Since in contrast to conventional rotating anode x-ray tubes, the anode and the cathode in rotating bulb tubes are directly mechanically connected to one another via the high-voltage insulator as well as via the vacuum tube, a cathode-side drive of the rotating bulb tube is possible without further measures. This means that the anode-side spacing from the focal spot to the corresponding end of the x-ray source is determined only by the thickness of the anode, the insulating distance between the anode and the inside of the protective housing of the x-ray source surrounding the rotating bulb tube, as well as by the wall thickness of the protective housing. An extremely short distance of the beam exit window from the corresponding end of the x-ray source, i.e. from the corresponding end of the protective housing, is thus possible, particularly when the rotating bulb tube is seated in the protective housing only at the cathode side, so that the structural length required at the anode side for the accommodation of a bearing implemented, for example, as a ball bearing can also be eliminated.

Given x-ray examination systems with a rotating bulb tube operable at low tube voltage and/or a power which is not too high, particularly in mammography, the rotating bulb tube, just like the protective housing of the x-ray source, can be at ground potential at the anode side. The distance between the focal spot or the beam exit window and the anode-side end of the x-ray source then can be very small since, due to the same potential of the anode and the protective housing of the x-ray source, no insulating distance but only a thin layer, approximately 1 mm, of a coolant needs to be present between the anode and the housing. Additionally or alternatively, the anode can be fashioned extremely thin, i.e. for example, thinner than 10 mm, since the thermal load on the anode is low.

DESCRIPTION OF THE PREFERRED EMBODIMENTS

Figure 1:
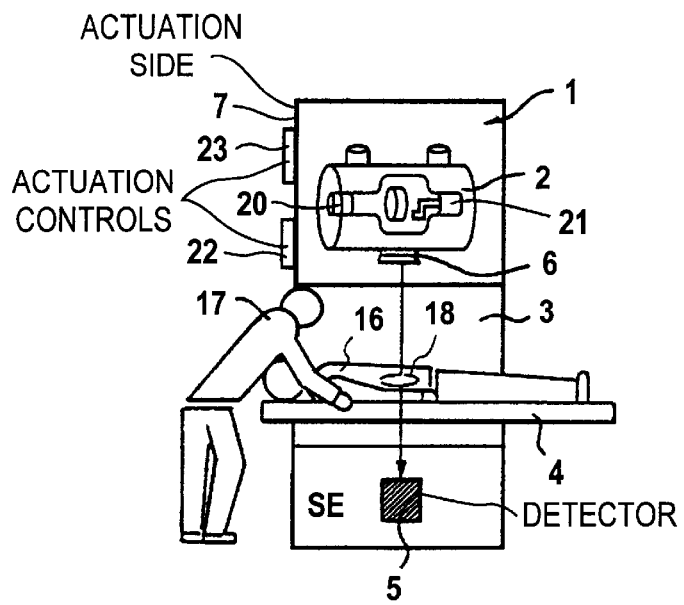
FIG. 1 shows a conventional x-ray examination system for computed tomography.

The conventional x-ray examination system for computed tomography shown in FIG. 1 has a gantry 1 in which an x-ray source 2 is displaceably seated so as to be rotatable around an opening 3 of the gantry 1. A support table 4 for a patient 16 extends such through the opening 3 so that a region 18 of interest in the patient 16 can be examined. When moving the x-ray source 2 around the opening 3, an x-ray detector offset by 180° relative to the x-ray source 2, i.e. arranged lying opposite the x-ray source 2, is co-rotated in a corresponding way.

As can be seen from FIG. 1, the x-ray source 2 of the arrangement according to the prior art contains a rotating anode x-ray tube 19 having high-voltage insulators 20, 21 at both sides, with the result that the beam exit window 6 of the x-ray source 2 is very far from both ends of a protective housing 9 of the x-ray source 2 surrounding the rotating anode x-ray tube 19. This causes the beam exit window 6 also to be far from the actuation side 7 of the x-ray examination system, i.e. that side of the gantry 1 at which the physician 17 is located for the preparation for the exposure and, possibly, during the implementation of an examination. The actuation side 7 is provided with control and display elements 22 and 23 schematically indicated in FIG. 1. That body region of the patient 16 in which the region 18 of interest for the respective examination is located is thus situated deep in the opening 3, and thus is difficult for the physician 17 to access.

Figure 2:
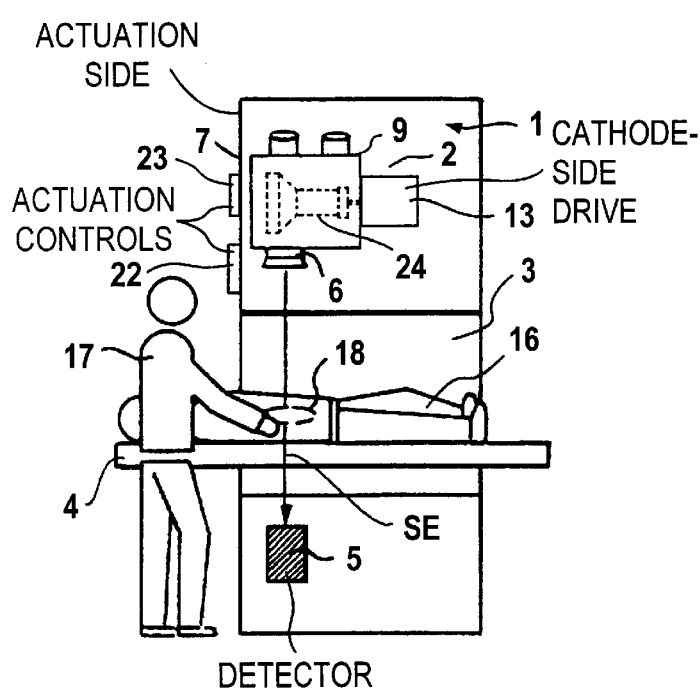
FIG. 2 shows an inventive x-ray system for computed tomography shown in an illustration corresponding to FIG. 1.
Figure 4:
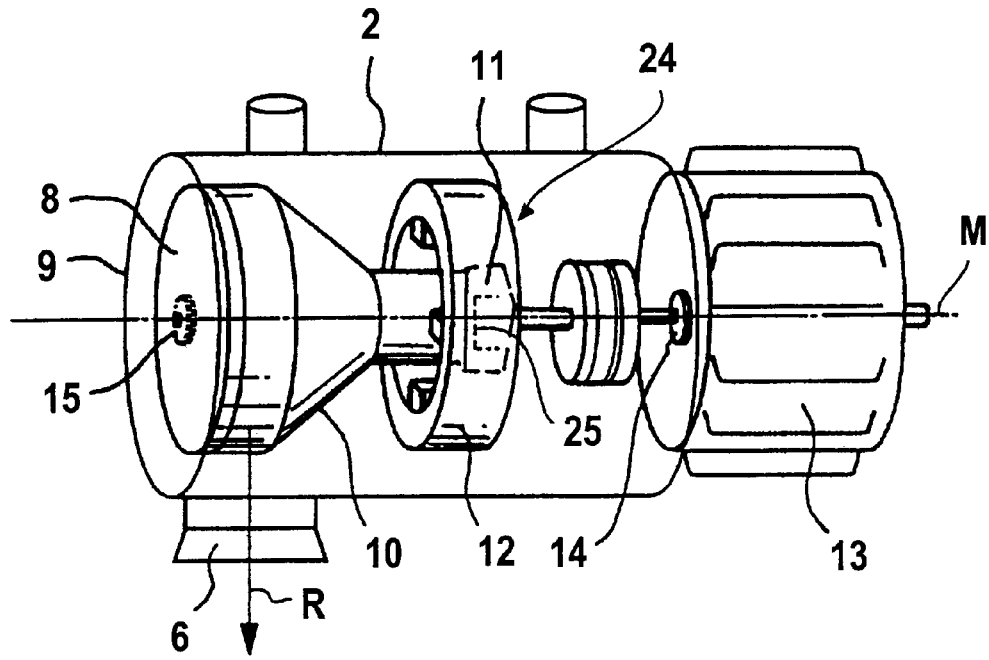
FIG. 4 shows a rotating bulb tube utilized in the computed tomography system according FIG. 2.

In the case inventive x-ray system according to FIG. 2 serving for computed tomography, an x-ray source 2 is employed having a rotating bulb tube 24, this rotating bulb tube 24 being known, for example, from U.S. Pat. No. 5,883,936 and thus being only schematically indicated in FIG. 2. Details of the structure thereof are shown in FIG. 4. The disclosure of U.S. Pat. No. 5,883,936 is incorporated into the present application by reference.

The rotating bulb tube 24 has a vacuum housing 10 rotatably mounted around the center axis M of the rotating bulb tube 24 with two bearings 14, 15, for example rolling bearings, particularly ball bearings. The vacuum housing 10 is disposed in a protective housing 9 filled with a liquid or gaseous, electrically insulating coolant, for example insulating oil, that is not shown in FIG. 4. The cathode 25 (indicated with broken lines in FIG. 4 ) of the rotating bulb tube 24 is attached to the vacuum housing 10 via a high-voltage insulator 11 at the one end of the vacuum housing 10. The anode 8 of the rotating bulb tube 24 is rigidly connected to the vacuum housing 10 and is located at the other end of the vacuum housing 10, opposite the cathode 25.

A magnet system 12 is provided between the cathode 25 and the anode 8. The magnet system 12 deflects and focuses the electron beam emanating, during operation of the rotating tube 24, from the cathode 25 onto a focal spot on the anode 8 that is stationary relative to the protective housing 9 of the x-ray source 2 and exhibits a defined spacing from the center axis M. The magnet system 12 surrounds a region of the vacuum housing 10 having a smaller diameter. The magnet system 12 may, for example, effect the focusing with a quadruple field and may effect the deflection of the electron beam with an additional dipole field. The x-rays emanating from the focal spot emerge from the vacuum housing 10—as indicated by the arrow R—through an x-ray-permeable region of the vacuum housing 10 and emerge from the protective housing 9 through a correspondingly positioned beam exit window 6.

The rotating bulb tube 24 has a cathode-side drive, which means that the drive motor 13 provided for the drive of the rotating bulb tube 24, which is preferably an electric motor, is attached to that end of the protective housing 9 that is adjacent to the cathode 25. In accordance with the invention the use of such a tube with a cathode-side drive allows the outside of the anode 8 of the rotating bulb tube 24 to be located in the immediate proximity of the other end of the protective housing 9.

As a result of this structure in the inventive system, the beam exit window 6 of the x-ray source 2 lies very close to the anode-side end of the protective housing 9. The x-ray source 2 thus can be installed such in the inventive x-ray examination system according to FIG. 2 so that the beam exit window 6 lies very close to the actuation side 7 of the gantry 1, so that the patient 16 is more easily accessible to the physician 17 then is the case given the x-ray examination system according to the prior art shown in FIG. 1.

The distance of the beam exit window 6 from the actuation side 7 can be further reduced when the rotating bulb tube 24 is seated in a correspondingly fashioned bearing 14 only at the cathode side, and the bearing at the anode side is eliminated. This possibility is illustrated in FIG. 4 with the bearing 15 is shown with broken lines.

It is thus clear that, even given two-pole operation of the rotating bulb tube 24, the exposure layer plane SE can lie close to the actuation side 7 of the gantry 1 since no high-voltage insulator is present at the anode side in the case of the rotating bulb tube 24.

Figure 3:
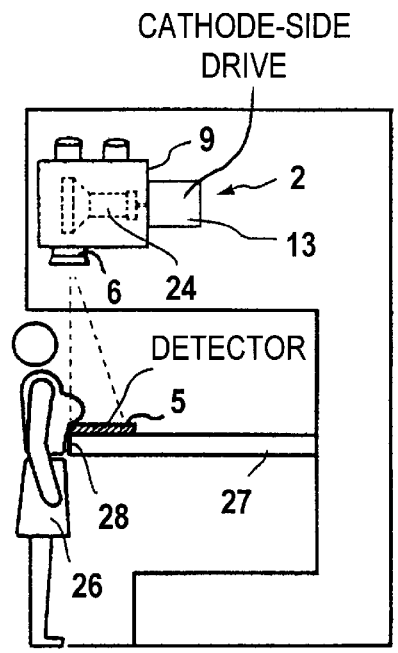
FIG. 3 shows an inventive x-ray examination system for mammography.

FIG. 3 shows an inventive x-ray diagnostic installation for mammography having a support 27 serving the purpose of supporting the breast of a patient 26 to be examined. An x-ray detector 5 is integrated into this in support 27 the region of its free end 28 at the side of the patient 26, i.e., the end neighboring the patient 26. A rotating bulb tube 24 is likewise provided as the x-ray source 2, this corresponding to the above-described rotating bulb tube 24 except for differences yet to be explained in conjunction with FIG. 5. The x-ray source 2 is installed into the x-ray diagnostic installation so that the anode 8 faces toward the patient-side end 28 of the support 27, and thus toward the exposure side of the x-ray diagnostic installation. The beam exit window 6 of the x-ray source 2 located close to the anode-side end of the protective housing 9 thus is situated approximately over the patient-side end 28 of the support 27, so that the breast tissue, as can be seen on the basis of the edge rays (shown with broken lines in FIG. 3) of the x-rays emerging from the beam exit window 6, is well-irradiated by the x-rays up to the base of the breast of the patient 26.

Figure 5:
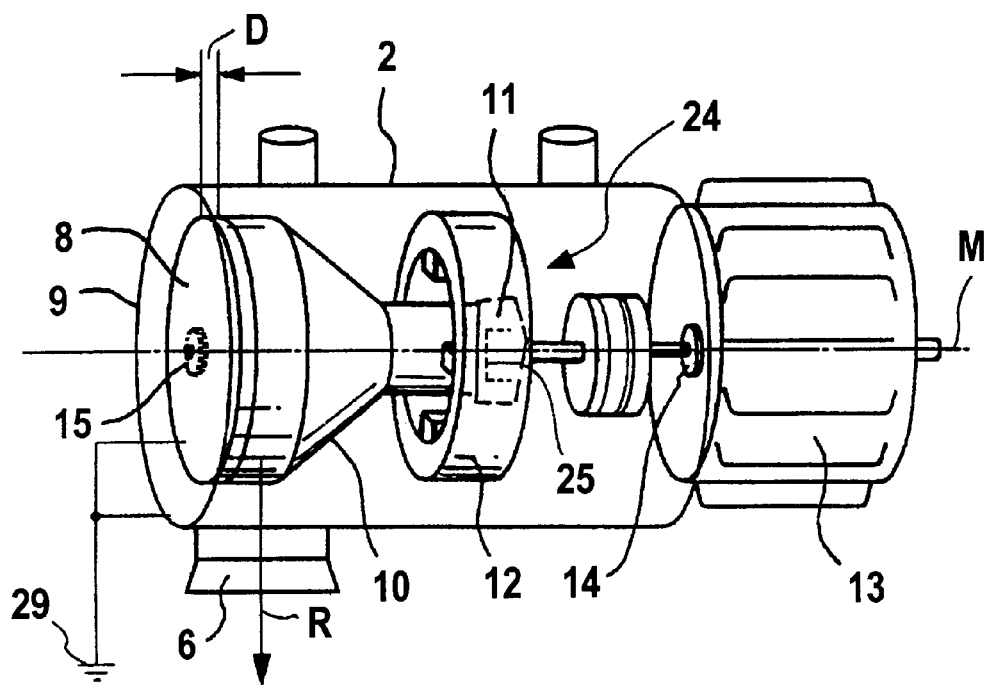
FIG. 5 shows a rotating bulb tube utilized in a mammography system according to FIG. 3.

Given single-pole operation as is usually adequate for mammography, the anode 8 of the rotating bulb tube 24 and the protective housing 9 of the x-ray source 2 are at ground potential 29, as illustrated in FIG. 5. As a result thereof, the distance between the exit window 6 and that end of the protective housing 9 neighboring the anode is reduced further, since a gap of only approximately 1 mm, in which coolant is present, exists between the wall forming the anode-side end of the protective housing 9 and the side of the anode 8 facing away from the cathode 25.

In view of the low thermal stress of the anode 8 in mammography, the anode 8 also has a thickness D of approximately 10 mm, allowing an additional reduction of the distance between the beam exit window 6 and that end of the protective housing 9 neighboring the anode 8.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray examination system comprising:
   an installation unit having an actuation side at which actuation controls are located; and
   a rotating bulb x-ray tube having a cathode-side drive, and having an anode, disposed inside of said installation unit with said anode of said rotating bulb x-ray tube facing toward said actuation side of said installation unit.

2. An x-ray examination system as claimed in claim 1 wherein said installation unit comprises a gantry for computed tomography.

3. An x-ray examination system as claimed in claim 1 wherein said anode is at ground potential.

4. An x-ray examination system as claimed in claim 1 further comprising a housing containing said rotating bulb tube and a fluid coolant contained in said housing, said housing having a housing wall adjacent said anode with a spacing of approximately 1 mm between said anode and said housing wall.

5. An x-ray examination system as claimed in claim 1 wherein said installation unit comprises a mammography unit having a support for a female breast at said exposure side.

6. An x-ray examination system comprising:

an installation unit having an exposure side adapted for positioning a patient at said exposure side; and a rotating bulb x-ray tube having a cathode-side drive, and having an anode, said anode facing toward said exposure side of said installation unit.

7. An x-ray examination system as claimed in claim 6 wherein said anode is at ground potential.

8. An x-ray examination system as claimed in claim 6 further comprising a housing containing said rotating bulb tube and a fluid coolant contained in said housing, said housing having a housing wall adjacent said anode with a spacing of approximately 1 mm between said anode and said housing wall.

9. An x-ray examination system as claimed in claim 6 wherein said anode has a thickness of less than 10 mm.

* * * * *